United States Patent
Horiuchi et al.

(10) Patent No.: US 8,531,658 B2
(45) Date of Patent: Sep. 10, 2013

(54) MEASURING CHIP DEVICE USING MAGNETS FOR INSTALLATION/REMOVAL

(75) Inventors: Tsutomu Horiuchi, Atsugi (JP); Toru Miura, Atsugi (JP); Yuzuru Iwasaki, Atsugi (JP); Michiko Seyama, Atsugi (JP); Tsuyoshi Hayashi, Atsugi (JP); Jun-ichi Takahashi, Atsugi (JP); Tsuneyuki Haga, Atsugi (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 347 days.

(21) Appl. No.: 13/125,279

(22) PCT Filed: Oct. 28, 2009

(86) PCT No.: PCT/JP2009/005704
§ 371 (c)(1),
(2), (4) Date: Apr. 20, 2011

(87) PCT Pub. No.: WO2010/050203
PCT Pub. Date: Jun. 5, 2010

(65) Prior Publication Data
US 2011/0194116 A1      Aug. 11, 2011

(30) Foreign Application Priority Data
Oct. 30, 2008   (JP) ................................. 2008-279671

(51) Int. Cl.
*G01N 21/01*       (2006.01)
(52) U.S. Cl.
USPC ............................ 356/244; 356/246; 356/445
(58) Field of Classification Search
USPC ................... 356/346, 445, 244; 29/559, 721
See application file for complete search history.

(56) References Cited

U.S. PATENT DOCUMENTS

| | | | |
|---|---|---|---|
| 2007/0022813 A1* | 2/2007 | Kasajima | 73/514.31 |
| 2007/0110424 A1* | 5/2007 | Iijima et al. | 396/133 |
| 2008/0018888 A1* | 1/2008 | Emilsson | 356/244 |
| 2008/0204745 A1* | 8/2008 | Sloyer et al. | 356/317 |

FOREIGN PATENT DOCUMENTS

| | | |
|---|---|---|
| JP | 2001-194298 A | 7/2001 |
| JP | 2001-272330 A | 10/2001 |
| JP | 2002-214131 A | 7/2002 |
| JP | 2002-243637 A | 8/2002 |

(Continued)

OTHER PUBLICATIONS

European Search Report, Patent Application No. 09823316.6, Jan. 3, 2013.

*Primary Examiner* — Tarifur Chowdhury
*Assistant Examiner* — Michael P Lapage
(74) *Attorney, Agent, or Firm* — Harness, Dickey & Pierce, P.L.C.

(57) ABSTRACT

A measuring chip installation/removal device of the present invention secures and removes a measuring chip to and from the top surface of an SPR measurement device that measures a specimen in the measuring chip by surface plasmon resonance. The measuring chip installation/removal device includes: a chip carrier on which the measuring chip is mounted; a chip carrier guide that guides the chip carrier on the top surface; and a first magnet provided in the chip carrier, and a second magnet is provided in the chip carrier guide. Orientation of a magnetic force received by the first magnet from the second magnet is reversed by displacing the chip carrier guide, so that the chip carrier is secured to or removed from the top surface.

5 Claims, 14 Drawing Sheets

(56) References Cited

FOREIGN PATENT DOCUMENTS

| JP | 3356212 B | 12/2002 |
| JP | 2005-315830 A | 11/2005 |
| WO | 2007/029895 A1 | 3/2007 |

* cited by examiner

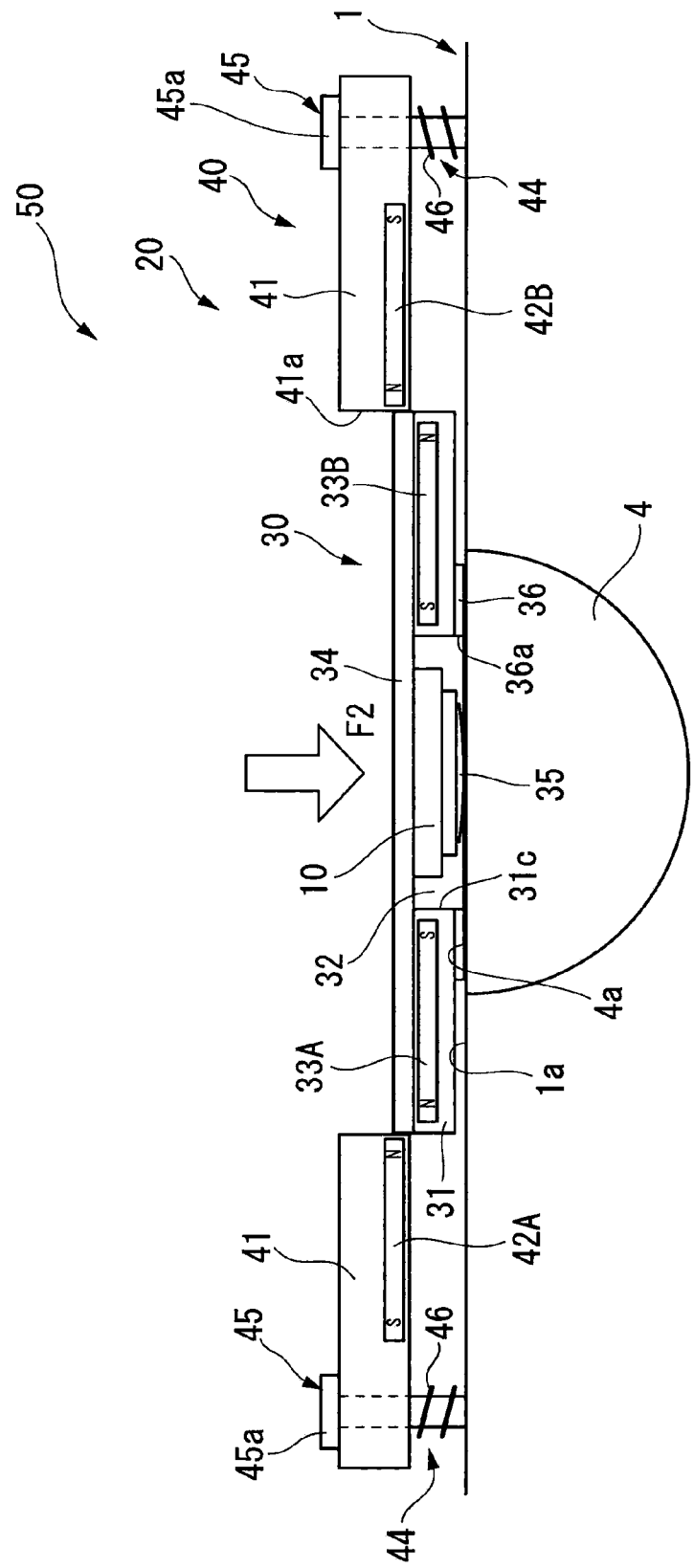

MEASURING CHIP DEVICE USING
MAGNETS FOR INSTALLATION/REMOVAL

TECHNICAL FIELD

The present invention relates to a measuring chip installation/removal device for securing and removing a measuring chip to or from the top surface of a surface plasmon resonance (SPR) measurement device for measuring a specimen in a measuring chip by surface plasmon resonance, an SPR measurement device in which it is installed, and a measuring chip installation/removal method in which the measuring chip installation/removal device is used.

Priority is claimed on Japanese Patent Application No. 2008-279671, filed Oct. 30, 2008, the content of which is incorporated herein by reference.

BACKGROUND ART

In clinical testing for evaluating the state of illness, and in environmental measurement for measuring the state of nitrogen oxide, ozone and the like, measurements using immunoassay and color reaction are typically used. In recent years, in those measurement methods, a measurement technique using surface plasmon resonance has been developed and come into practical use (for example, refer to Patent Documents 1 and 2). This measurement technique uses resonance between an evanescent wave and a surface plasmon wave on the surface of a metal with which a specimen of an object to be measured is in contact.

Measurement using surface plasmon resonance, as shown in FIG. 11 for example, is performed using an SPR measurement device 1, which includes a light source 2, an incident side lens 3, a prism 4, and a light detecting section 5. A square planar measuring chip 10 is fixed on a measurement face 4$a$, which is the top surface of the prism 4 of the SPR measurement device 1. A metal thin film (Au thin film) 11 is adhered to the substrate 10$a$ of the measuring chip 10, as shown in FIG. 12 in detail. A specimen, being an object to be measured, is in contact with the metal thin film 11.

A light injected from the light source 2 is collected by the incident side lens 3, and the light is injected into the prism 4 and irradiated onto the measuring chip 10 on the measurement face 4$a$ of the prism 4. The light that irradiates the measuring chip 10 passes through the substrate 10$a$ of the measuring chip 10 as shown in FIG. 12 in detail, and is reflected by the metal thin film 11. The intensity of the reflected light is measured by the light detecting section 5 configured by an imager such as a so-called CCD image sensor or the like. By such measurement, as shown in FIG. 13, a valley is observed in which the reflection coefficient becomes extremely low at the angle at which the above resonance occurs.

As described above, in the SPR measurement device 1, light arrives at and departs the measurement face 4$a$ of the prism 4 and the measuring chip 10. At this time, in order to suppress the refraction and reflection of the light at the boundary between the measurement face 4$a$ and the measuring chip 10, it is necessary for the refractive indexes of the prism 4 and the measuring chip 10 to match, and to adhere the measuring chip 10 to the measurement face 4$a$ completely.

However, even though the refractive indexes of the prism 4 and the measuring chip 10 can be matched easily by material selection or the like, it is not easy to adhere the two completely without any gap. Therefore, matching oil (refractive index matching agent) whose refractive index matches them is normally intervened between the prism 4 and the measuring chip 10. By so doing, refraction and reflection of the light in the boundary between the prism 4 and the measuring chip 10 are suppressed.

Normally, in SPR measurement, antibodies and DNA conditional on the objective substance to be detected, are fixed in advance on the metal thin film 11 of the measuring chip 10. When a specimen solution in which the objective substance exists is introduced into the chip, the objective substance is captured by the stabilized substance, and detected as a signal change of the SPR measurement device 1. It is not easy to desorb the objective substance once captured by the stabilized substance completely, and accurate measurement is difficult in repeated measurements using the same measuring chip 10. Especially, in the case where medical treatment or food evaluation is intended, in order to avoid contamination between specimens, it is desirable to use the measuring chip 10 only once. From this point, the frequency of exchange of measuring chips 10 with respect to the SPR measurement device 1 is extremely high.

Incidentally, in the case where the measuring chip 10 is adhered using matching oil, it is not easy to remove the measuring chip 10 from the SPR measurement device 1. Furthermore, it is also not easy to remove the matching oil completely from the measuring chip 10 and the measurement face 4$a$ of the prism 4.

Therefore, it is not possible to exchange measuring chips 10 smoothly, which hinders efficient measurement. Moreover, it is necessary to use a matching oil absorber in order to remove the matching oil. Consequently problems occur in terms of cost and waste management.

Therefore, in order to deal with this, Patent Document 3 proposes a method for fixing the measuring chip 10 on the SPR measurement device 1 using matching film instead of matching oil.

PRIOR ART DOCUMENTS

Patent Documents

[Patent Document 1] Japanese Unexamined Patent Application, First Publication No. 2001-194298
[Patent Document 2] Japanese Unexamined Patent Application, First Publication No. 2002-214131
[Patent Document 3] Japanese Patent No. 3356212

SUMMARY OF THE INVENTION

Problem to be Solved by the Invention

However, in the case where a matching film as shown in the above-described Patent Document 3 is used, it is difficult to prevent air from intruding between the measuring chip and the matching film, and between the matching film and the prism. Furthermore, the measuring chip needs to be pressed down on the measurement face of the prism. Moreover, when it is pressed down, it is not easy to maintain the parallelism of the measuring chip and the measurement face of the prism in a state in which a matching film is sandwiched between them. Therefore, there is a problem in that measuring chips cannot be exchanged smoothly.

The present invention has been made in view of such problems, and an object thereof is to provide a measuring chip installation/removal device, an SPR measurement system, and a measuring chip installation/removal method, whereby a measuring chip can be installed and removed easily to and from the top surface of an SPR measurement device, and measuring chips can be exchanged easily.

Means for Solving the Problem

In order to solve the above problems, this invention proposes the following measures.

A measuring chip installation/removal device of the present invention secures and removes a measuring chip to and from the top surface of an SPR measurement device that measures a specimen in the measuring chip by surface plasmon resonance. The measuring chip installation/removal device includes: a chip carrier on which the measuring chip is mounted; a chip carrier guide that guides the chip carrier on the top surface; and a first magnet provided in the chip carrier, and a second magnet provided in the chip carrier guide. Orientation of a magnetic force received by the first magnet from the second magnet is reversed by displacing the chip carrier guide, so that the chip carrier is secured to or removed from the top surface.

According to the measuring chip installation/removal device with such characteristics, by displacing the chip carrier guide on which the second magnet is mounted, the orientation of the magnetic force received by the first magnet is reversed in an appropriate direction, so that it is possible for the measuring chip 10 to be installed and removed easily.

That is, when the measuring chip is secured to the top surface of the SPR measurement device, it is possible to make the first magnet of the chip carrier, on which the measuring chip is mounted, generate a downward magnetic force, and adhere the chip carrier to the top surface. Furthermore, when removing the measuring chip, by displacing the chip carrier, it is possible to make the first magnet generate an upward magnetic force, and detach it from the top surface easily. As a result, it is possible to install and remove the measuring chip to and from the top surface of the SPR measurement device easily.

Moreover, in the measuring chip installation/removal device according to the present invention, the chip carrier guide may have a plate shape extending along the top surface, and may have a guide hole which passes through the chip carrier guide in a thickness direction thereof, and in which the chip carrier is inserted, and the chip carrier guide may be movable between a first position at which it is separated upwards from the top surface, and a second position that is close to the top surface.

According to the measuring chip installation/removal device with such characteristics, by inserting the chip carrier into the guide hole of the chip carrier guide, it is possible to locate the chip carrier at a home position on the SPR measurement device. As a result, it is possible to position the measuring chip on the top surface of the SPR measurement device easily.

Moreover, by moving the chip carrier guide between the first position and the second position selectively, it is possible to reverse the orientation of the magnetic force generated in the first magnet of the chip carrier, so that it is possible to secure and remove the chip carrier to and from the top surface more smoothly.

Furthermore, in the measuring chip installation/removal device according to the present invention, the magnetic force may be a repulsive force generated between the first magnet and the second magnet.

As a result, when securing the measuring chip on the top surface of the SPR measurement device, it is possible to adhere the measuring chip to the top surface by a downward repulsive force generated in the first magnet of the chip carrier. Moreover, when removing the measuring chip, it is possible to detach the chip carrier from the top surface easily by an upward repulsive force generated in the first magnet.

If it is attempted to secure and remove the measuring chip using an attracting force for example, the attracting force generated when the first magnet and the second magnet approach and make contact is great. Therefore it is difficult to separate the two magnets. On the other hand, if the two magnets are separated in order to avoid such a situation, the attracting force becomes inadequately small, so a situation can occur in which the measuring chip cannot be secured. Moreover, in the case where a plurality of each of the first and second magnets is installed, if the magnitude of the attracting forces is unbalanced, only one of the pairs of magnets makes contact, so that it is difficult to maintain the parallelism of the chip carrier with respect to the top surface of the SPR measurement device.

Regarding this point, in the case where a repulsive force is used, it is easy to balance the forces generated between the two magnets. Therefore it is possible to secure and remove the measuring chip stably and reliably.

Moreover, in the measuring chip installation/removal device according to the present invention, there may be provided an energizing member that urges the chip carrier guide toward the first position from the second position, the second magnet of the chip carrier guide in the first position may be located above the first magnet of the chip carrier mounted on the top surface, and the second magnet of the chip carrier guide in the second position may be located below the first magnet of the chip carrier mounted on the top surface.

In the measuring chip installation/removal device with such characteristics, if it is attempted to insert the chip carrier into the guide hole of the chip carrier guide, an upward repulsive force is generated in the first magnet of the chip carrier guide. If the chip carrier is inserted into the guide hole against this repulsive force, and the chip carrier is mounted on the top surface of the SPR measurement device, in this state, since the first magnet is located below the second magnet, a downward repulsive force is generated in the first magnet. As a result, it is possible to adhere the chip carrier to the top surface of the SPR measurement device.

On the other hand, when removing the chip carrier from the top surface, the chip carrier guide is moved to the second position from the first position against the urging of the energizing member. By so doing, the second magnet of the chip carrier guide is located below the first magnet of the chip carrier, and hence an upward repulsive force is generated in the first magnet. As a result, it is possible to detach the chip carrier from the top surface of the SPR measurement device easily.

Moreover, in the measuring chip installation/removal device according to the present invention, the chip carrier may include a chip case in which the measuring chip is secured, and a magnet case that is located at a side of the chip case, and that retains the first magnet such that it slide and project in a horizontal direction, and when the repulsive force is generated in the first magnet, the first magnet may slide so as to enter a concave groove provided in a side face of the chip case.

In a measuring chip installation/removal device with such characteristics, when measurement is not being performed, the chip carrier can be separated into the chip case and the magnet case. On the other hand, when mounting the chip carrier on the top surface of the SPR measurement device, by the first magnet being inserted into the concave groove in the chip case by a repulsive force, the chip case and the magnet case are secured together.

Consequently handling of the chip carrier when measurement is not being performed can be improved, and also it is possible to position and lock the measuring chip and the SPR measurement device easily when measurement is being performed.

An SPR measurement system according to the present invention includes the SPR measurement device on which any one of the above-described measuring chip installation/removal device is mounted.

As a result, it is possible to exchange measuring chips easily as described above.

A measuring chip installation/removal method according to a first aspect of the present invention uses the above-described measuring chip installation/removal device, and includes: inserting the chip carrier into the guide hole of the chip carrier guide against a repulsive force generated in the first magnet, and securing the measuring chip on the top surface by a downward repulsive force generated in the first magnet during the insertion; and moving the chip carrier guide to the second position from the first position against urging of the energizing member in a state where the measuring chip is secured on the top surface, and separating the measuring chip from the top surface by an upward repulsive force generated in the first magnet.

According to such a method of installation and removal of a measuring chip, it is possible to generate a repulsive force in an appropriate direction in the first magnet of the chip carrier. Therefore, the chip carrier on which the measuring chip is mounted can be adhered to and detached from the top surface of the SPR measurement device easily, so that it is possible to exchange measuring chips smoothly.

A measuring chip installation/removal method according to a second aspect of the present invention uses the above-described measuring chip installation/removal device, and includes: inserting the chip carrier into the guide hole of the chip carrier guide against a repulsive force generated in the first magnet, inserting the first magnet into the concave groove by sliding the first magnet by a horizontal repulsive force generated in the first magnet during the insertion, and securing the measuring chip on the top surface by a downward repulsive force generated in the first magnet; and moving the chip carrier guide to the second position from the first position against urging of the energizing member in a state where the measuring chip is secured on the top surface, and separating the measuring chip from the top surface by an upward repulsive force generated in the first magnet.

According to such a measuring chip installation/removal method, similarly to the above, it is possible to exchange measuring chips smoothly. Moreover, the handling of the chip carrier when measurement is not being performed can be improved, and also it is possible to position and lock the measuring chip and the SPR measurement device easily when measurement is being performed.

Effect of the Invention

According to the measuring chip installation/removal device, the SPR measurement device, and the measuring chip installation/removal method of the present invention, by making a chip carrier on which a measuring chip is mounted generate a magnetic force in an appropriate direction, the measuring chip can be installed on and removed from the top surface of the SPR measurement device easily, so that it is possible to exchange measuring chips easily.

BRIEF DESCRIPTION OF THE DRAWINGS

FIG. 7 is a sectional side elevation of the SPR measurement system of the first modified example of the first embodiment.

EMBODIMENTS FOR CARRYING OUT THE INVENTION

Hereunder is a detailed description of a first embodiment of a measuring chip installation/removal device, an SPR measurement system, and a measuring chip installation/removal method, according to the present invention with reference to FIG. 1 to FIG. 5.

Figure 1:
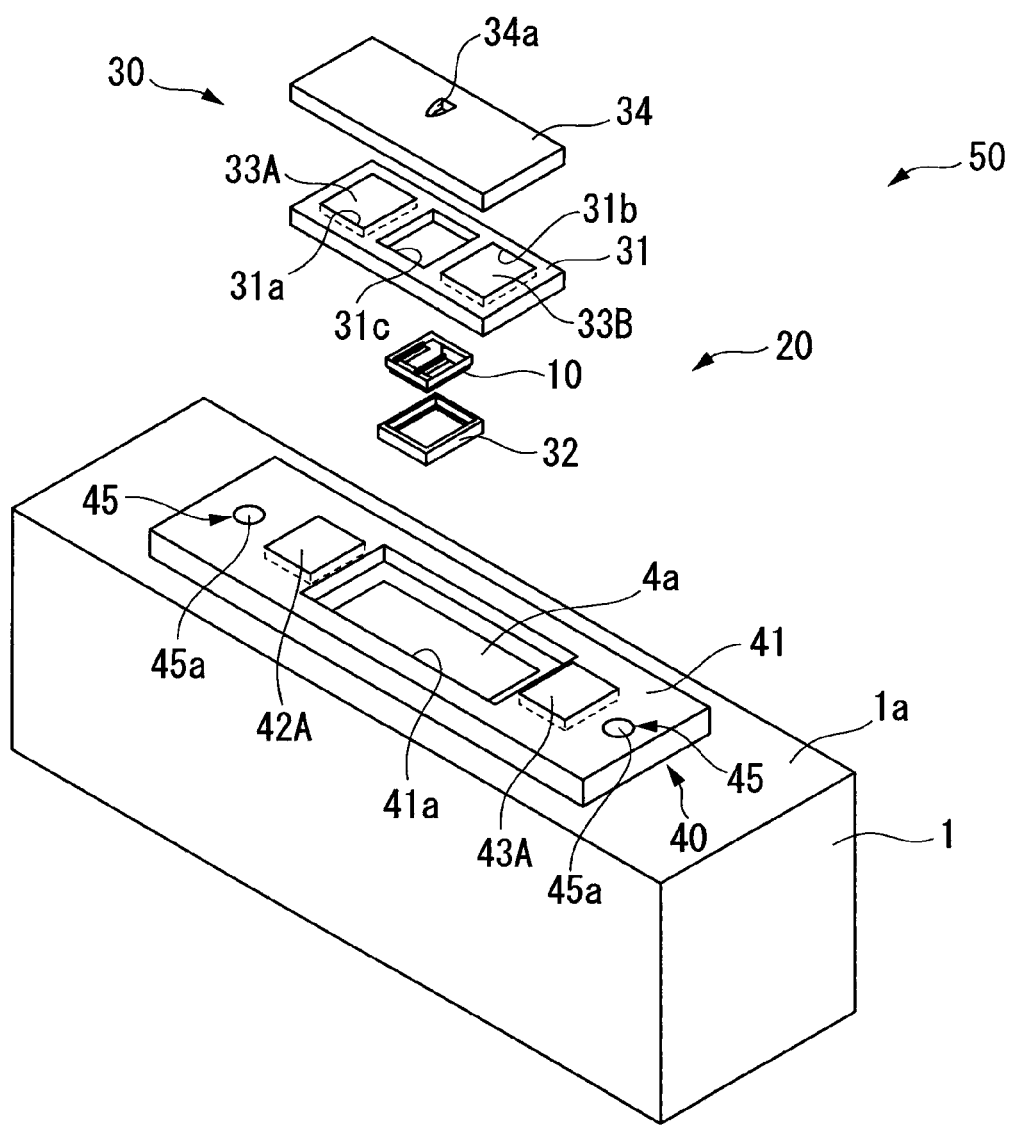
FIG. 1 is an exploded perspective view of an SPR measurement system of a first embodiment.

FIG. 1 is an exploded perspective view of the SPR measurement system of the first embodiment. FIG. 2 to FIG. 5 are enlarged views of sectional side elevations of the main parts of the SPR measurement system.

Figure 2:
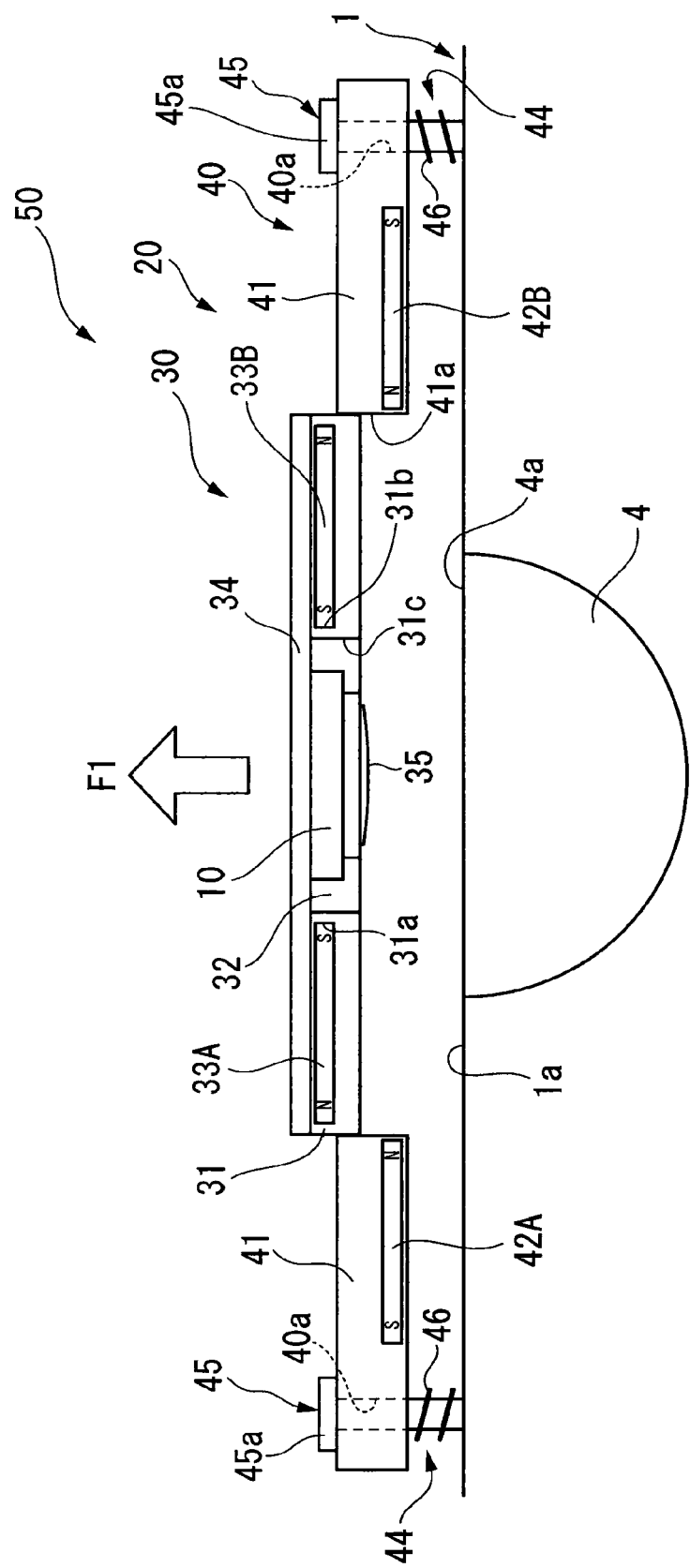
FIG. 2 is an enlarged view of a sectional side elevation of the main parts of the SPR measurement system of the first embodiment.

As shown in FIG. 1 and FIG. 2, in an SPR measurement system 50, a measuring chip installation/removal device 20 is installed on the top surface 1a of an SPR measurement device 1. The measuring chip installation/removal device 20 includes a chip carrier 30 and a chip carrier guide 40. A measuring chip 10 is loaded in the chip carrier 30. The chip carrier guide 40 guides the chip carrier 30 to the top surface 1a of the SPR measurement device 1.

Figure 11:
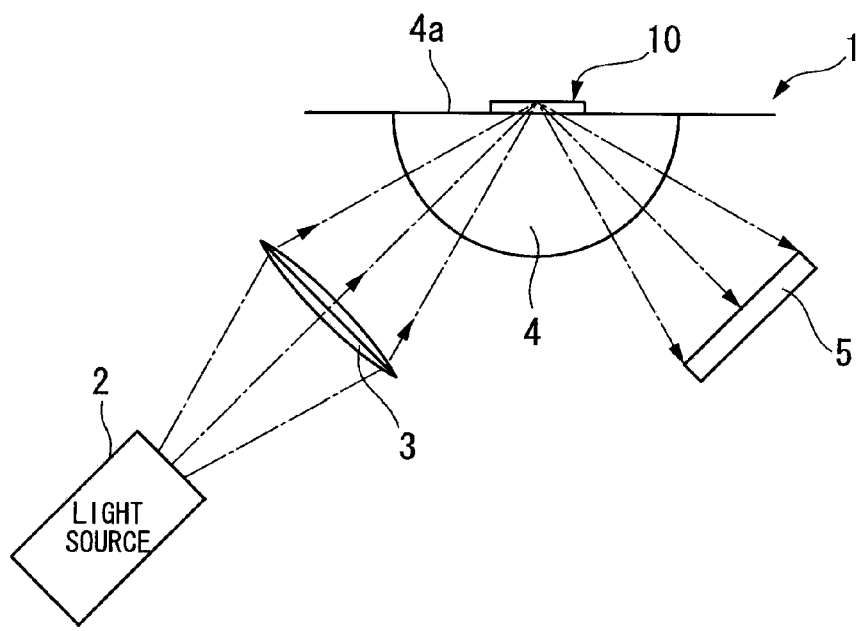
FIG. 11 is a schematic block diagram of an SPR measurement device.
Figure 12:
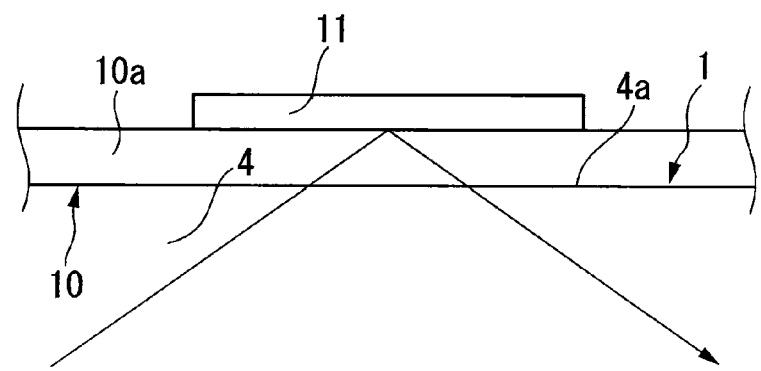
FIG. 12 is an enlarged diagram of the main part of the measuring chip of FIG. 11.
Figure 13:
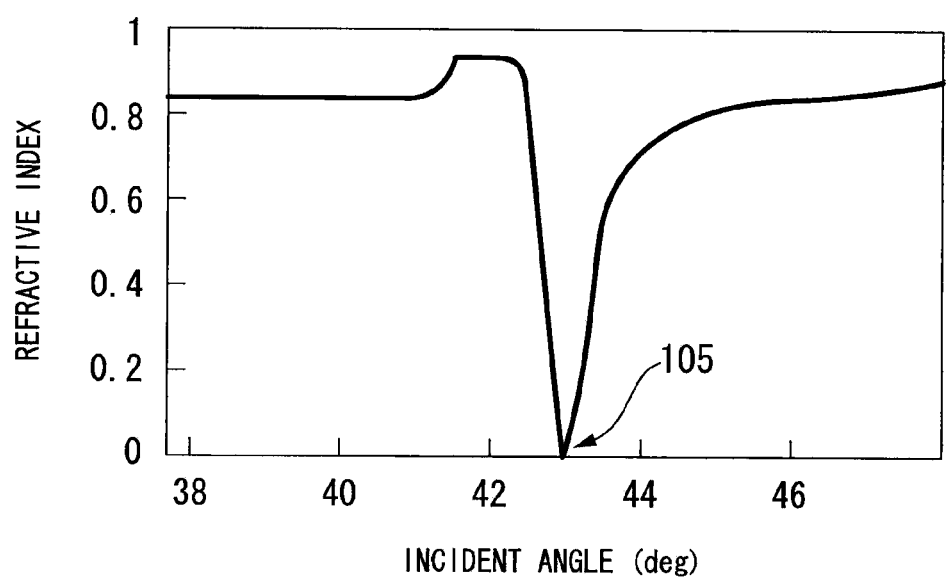
FIG. 13 is a characteristic diagram to explain the relationship between reflection coefficient and reflection angle of a detecting section, as measured by an SPR measurement device.

The constructions of the SPR measurement device 1 and the measuring chip 10 are as described above. As shown in FIG. 11 and FIG. 12, a light, which is injected from a light source 2 of the SPR measurement device 1 and collected by an incident side lens 3, is irradiated onto the measuring chip 10 positioned on a measurement face 4a of a prism 4. The light reflected by a metal film 11 on the measuring chip 10 is measured by a light detecting section 5. As a result, at the angle at which resonance occurs between an evanescent wave and a surface plasmon wave on the surface of the metal film 11 with which a specimen of an object to be measured is in contact, a valley is observed in which the reflection coefficient becomes extremely low, as shown in FIG. 13 for example.

The chip carrier 30, as shown in FIG. 1 and FIG. 2, are configured by a housing 31, a chip case 32, two first magnets 33A and 33B, and a lid 34.

The housing 31 is a plate approximately rectangular in plan view. Cavities 31a and 31b that are approximately square in plan view are formed in the housing 31 at both ends in the longitudinal direction. A through hole 31c is formed between the pair of cavities 31a and 31b, that is, in the center, in the longitudinal direction, of the housing 31. The through hole 31c is square in plan view, and passes through the housing 31 in the thickness direction.

First magnets 33A and 33B, which are plates formed approximately square, are fitted into the cavities 31a and 31b of the housing 31. The first magnets 33A and 33B, as shown in FIG. 2, are arranged with symmetrical magnetic orientations such that their south poles point to the central part in the longitudinal direction of the housing 31, and their north poles point to the ends in the longitudinal direction of the housing 31.

The chip case 32 is inserted into the through hole 31c of the housing 31. The chip case 32 is a square frame in plan view, and is formed such that the measuring chip 10 is retained inside. When the chip case 32 is inserted into the housing 31, the bottom face of the measuring chip 10 is flush with the bottom face of the housing 31, and is exposed from the housing 31.

In a state in which the first magnets 33A and 33B, and the chip case 32, which retains the measuring chip 10, are inserted into the housing 31 as described above, the lid 34 is fitted on the housing 31. An introduction hole 34a passing through the lid 34 in the thickness direction, is formed in the center in plan view of the lid 34. A specimen is introduced into the measuring chip 10 in the chip carrier 30 from the introduction hole 34a.

The chip carrier 30 with such a construction is mounted on the top surface 1a of the SPR measurement device 1 by being guided by the chip carrier guide 40 during measurement, such that the measuring chip 10 whose bottom face is exposed, is located on the measurement face 4a.

The chip carrier guide 40, as shown in FIG. 1 and FIG. 2, are configured by a chip carrier guide body 41 and two second magnets 42A and 42B.

The chip carrier guide body 41 is a plate approximately rectangular in plan view. A guide hole 41a is formed in the center in plan view of the chip carrier guide body 41. The guide hole 41a is approximately rectangular in plan view, with its longitudinal direction and transverse direction matching the external shape of the chip carrier guide body 41, and passes through the chip carrier guide body 41 in the thickness direction. The plan view shape of the guide hole 41a is approximately the same as the plan view shape of the chip carrier 30. As a result, it is possible for the chip carrier 30 to fit in the guide hole 41a without any gap.

The second magnets 42A and 42B are embedded at the two ends in the longitudinal direction of the guide hole 41a of the chip carrier guide 40. The second magnets 42A and 42B, as shown in FIG. 2, are arranged with symmetrical magnetic orientations such that their north poles point to the central part in the longitudinal direction of the chip carrier guide body 41, and their south poles point to the ends in the longitudinal direction of the chip carrier guide body 41.

Such a chip carrier guide 40 is placed parallel with the top surface 1a of the SPR measurement device 1. To be specific, the chip carrier guide 40 is placed in a location where the measuring chip 10 exposed on the bottom face of the chip carrier 30 is located on the measurement face 4a when the chip carrier 30 is fitted into the guide hole 41a.

Moreover, the chip carrier guide 40 can move between a first position (refer to FIG. 2 and FIG. 3) and a second position (refer to FIG. 4) by means of a movable mechanism 44. In the first position, the chip carrier guide 40 is separated by a fixed distance above the top surface 1a. In the second position, the chip carrier guide 40 is close to the top surface 1a.

Bolt insertion holes 40a (refer to FIG. 2) are formed in the chip carrier guide body 41, which pass through the chip carrier guide body 41 in the thickness direction in the vicinity of the two ends in the longitudinal direction. Bolts 45 are inserted downward into the bolt insertion holes 40a from above. The bottom ends of the bolts 45 are secured in the top surface 1a of the SPR measurement device 1. Furthermore, coil springs (energizing members) 46 are fitted externally to the parts of the bolts 45 between the chip carrier guide body 41 and the top surface 1a. The movable mechanism 44 is constructed in this manner.

By constructing in this manner, in a state in which no external force is applied to the chip carrier guide 40, the chip carrier guide 40 is urged upward by the coil springs 46, and restrained from upward movement by the heads 45a of the bolts 45. As a result, the chip carrier guide 40 settles in the first position where it is separated by a fixed distance above the top surface 1a of the SPR measurement device 1.

When external force is applied by pressing the top surface of the chip carrier guide 40 downward, the coil springs 46 are compressed, and the chip carrier guide 40 moves to the second position where it is close to the top surface 1a of the SPR measurement device 1.

Figure 3:
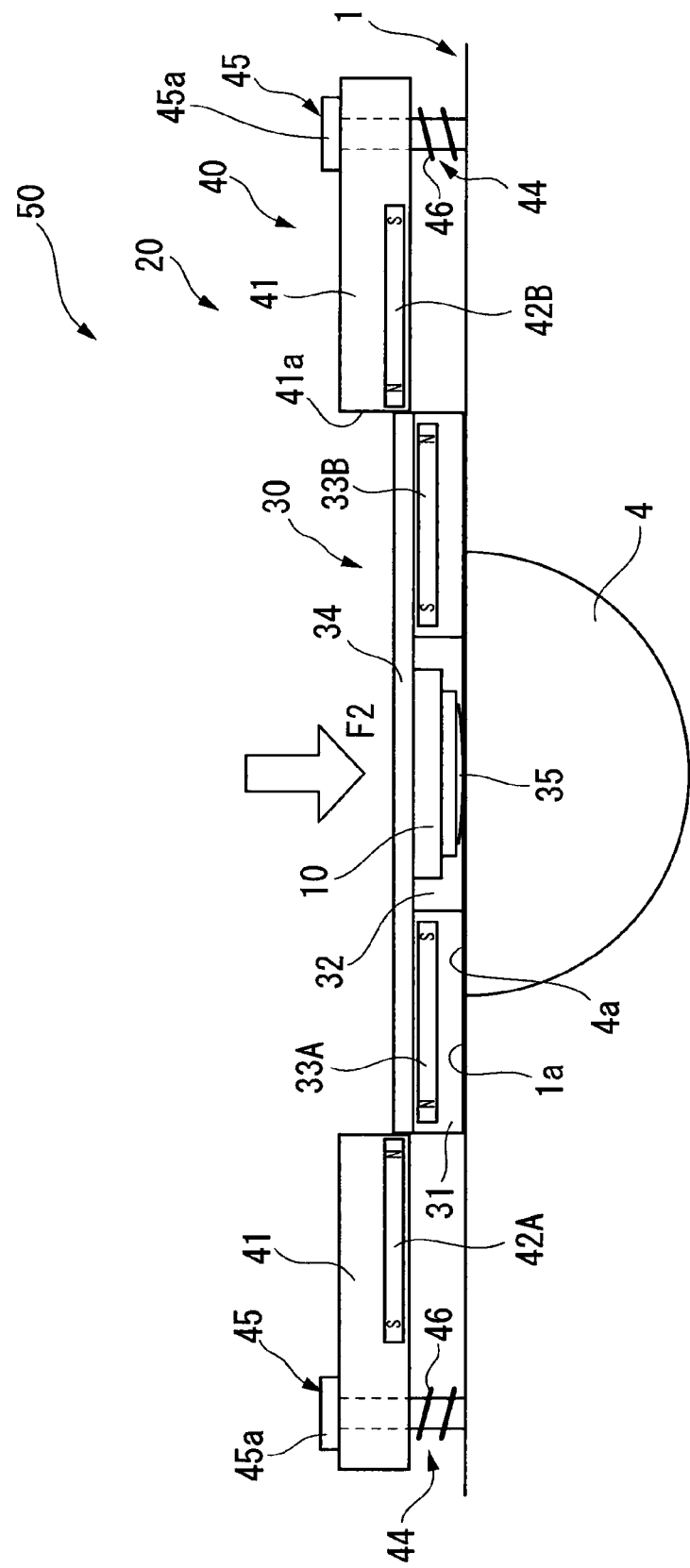
FIG. 3 is an enlarged view of the sectional side elevation of the main parts of the SPR measurement system of the first embodiment.

In the case where such a chip carrier guide 40 is located in the first position, as shown in FIG. 3, the second magnets 42A and 42B in the chip carrier guide 40 are located above the first magnets 33A and 33B in the chip carrier 30, which is mounted on the top surface 1a of the SPR measurement device 1.

Figure 4:
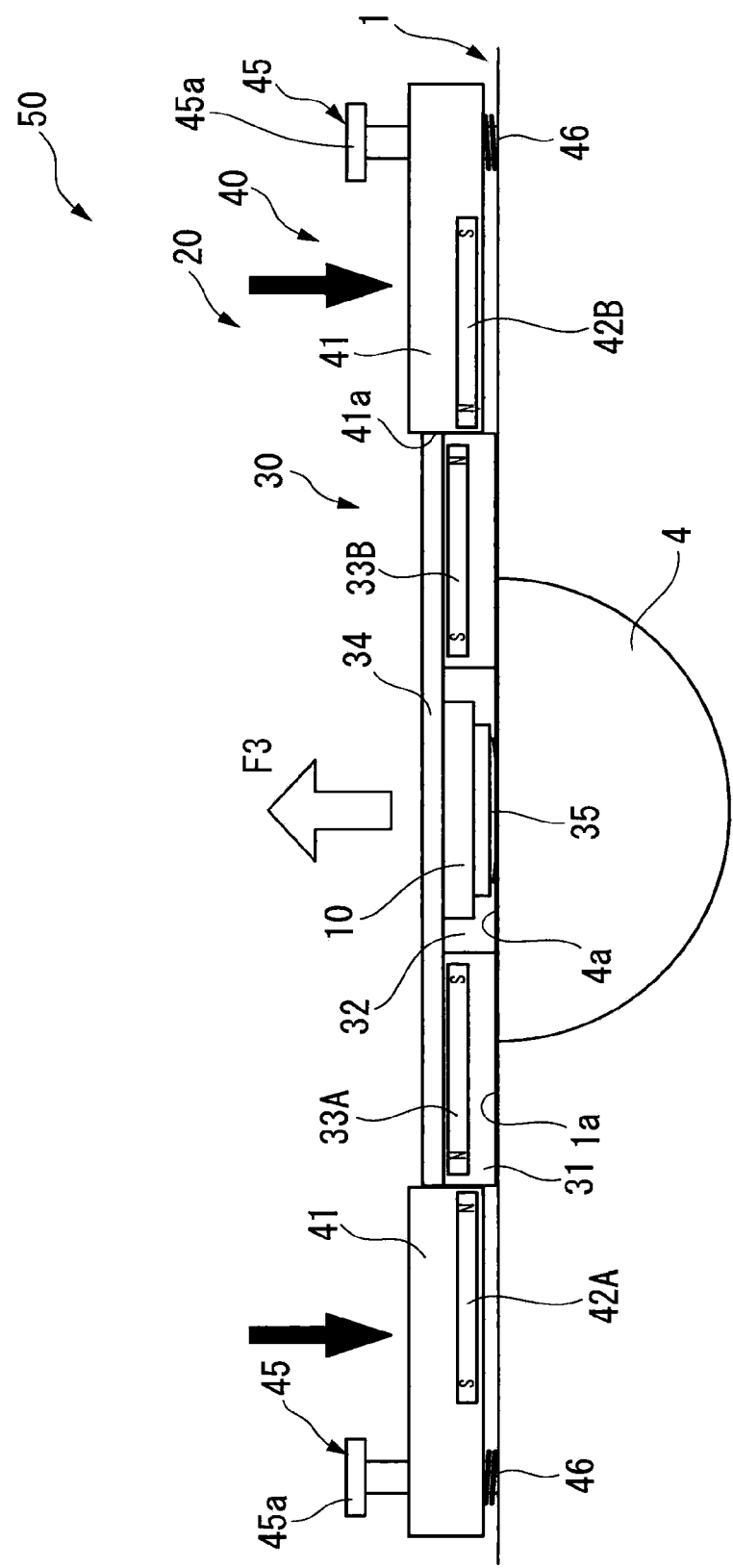
FIG. 4 is an enlarged view of the sectional side elevation of the main parts of the SPR measurement system of the first embodiment.

In the case where the chip carrier guide 40 is located in the second position, as shown in FIG. 4, the second magnets 42A and 42B are located below the position of the first magnets 33A and 33B in the chip carrier 30, which is mounted on the top surface 1a of the SPR measurement device 1.

Next is a description of a method of securing and removing the measuring chip 10 using the measuring chip installation/removal device 20 in the SPR measurement system 50 constructed as above.

When mounting the measuring chip 10 at a predetermined location on the top surface 1a of the SPR measurement device 1, firstly, a matching film 35 is adhered to the bottom of the measuring chip 10, and afterward, the measuring chip 10 is mounted in the chip carrier 30. At this time, the matching film 35 is exposed to the outside from the bottom face of the chip carrier 30.

The matching film 35 may be a film having the same refractive index as the prism 4 of the SPR measurement device 1 and the measuring chip 10. The matching film 35 is generated, for example, by forming a solution, in which a plasticizer is added to polyvinyl chloride, into a film using a casting method in which tetrahydrofuran solution is used.

Next, the chip carrier 30 in which the measuring chip 10 is mounted is lowered down into the guide hole 41a from above while being maintained in a parallel state to the horizontal surface such that it is inserted into the guide hole 41a of the chip carrier guide 40 located in the first position. As a result, by the operation of inserting the chip carrier 30 into the guide hole 41a, the chip carrier 30 is guided to a predetermined position on the top surface 1a of the SPR measurement device 1.

At this time, the two first magnets 33A and 33B in the chip carrier 30 approach the second magnets 42A and 42B of the chip carrier guide 40 respectively. As a result, an upward repulsive force is generated in the first magnets 33A and 33B due to the interaction of the north poles of the first magnets 33A and 33B and the north poles of the second magnets 42A and 42B. As a result, an upward force F1 acts on the chip carrier 30 as a whole.

The chip carrier 30 is lowered further downward against the upward force F1. By the downward movement, when it passes a location where the height of the first magnets 33A and 33B of the chip carrier 30 and that of the second magnets 42A and 42B of the chip carrier guide 40 are the same, the vertical position of the first magnets 33A and 33B is located below the vertical position of the second magnets 42A and 42B. As a result, a downward repulsive force is generated in the first magnets 33A and 33B. Due to this, when the chip carrier 30 is mounted on the top surface 1a of the SPR measurement device 1, as shown in FIG. 3, a downward force F2 acts on the chip carrier 30 as a whole, and the chip carrier 30 is pressed down on the top surface 1a. As a result, it is possible to prevent air from being trapped in the matching film, and furthermore, to mount the measuring chip 10 parallel to the measurement face 4a.

A method will now be described in which the chip carrier 30 and the measuring chip 10, which are mounted and secured on the top surface 1a of the SPR measurement device 1 in this manner, are removed from the top surface 1a. In order to remove the chip carrier 30 and the measuring chip 10, an external force is applied downward on the chip carrier guide 40 located at the first position, so that the chip carrier guide 40 is pressed downward against a repulsive force generated in the second magnets 42A and 42B and the energizing force of the coil springs 46. By so doing, when the chip carrier guide 40 is moved to the second position, the vertical position of the second magnets 42A and 42B of the chip carrier guide 40 is below the vertical position of the first magnets 33A and 33B of the chip carrier 30. As a result, an upward repulsive force is generated in the first magnets 33A and 33B. Due to this, as shown in FIG. 4, an upward force F3 acts on the chip carrier 30 as a whole, and hence it is possible for the chip carrier 30 to be detached and removed easily from the top surface 1a of the SPR measurement device 1.

Figure 5:
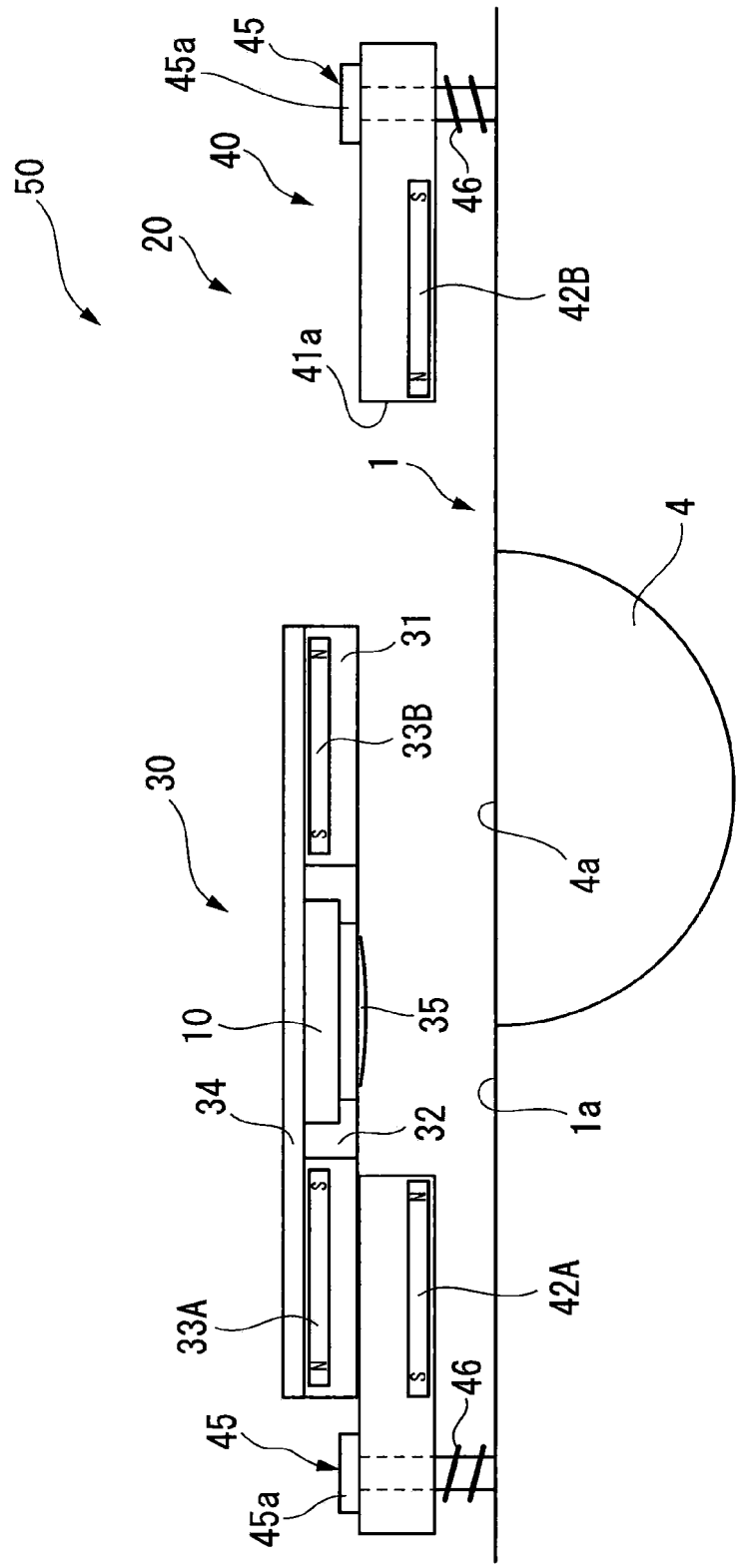
FIG. 5 is an enlarged view of the sectional side elevation of the main parts of the SPR measurement system of the first embodiment.

After the chip carrier 30 passes through the guide hole 41a of the chip carrier guide 40, and is separated, the chip carrier 30 is attracted by the magnetic force of either one of the second magnets 42A and 42B of the chip carrier guide 40. As a result, the chip carrier 30, as shown in FIG. 5, settles on one side of the carrier guide 40. Due to this, the chip carrier 30 does not jump far off the SPR measurement device 1, and the specimen in the measuring chip 10 does not splash and contaminate the surroundings.

As described above, according to the measuring chip installation/removal device 20 in the SPR measurement system 50 of the present embodiment, by displacing the chip carrier guide 40 on which the second magnets 42A and 42B are mounted, it is possible to install and remove the measuring chip 10 easily.

That is, when securing the measuring chip 10 on the top surface 1a of the SPR measurement device 1, it is possible to make the first magnets 33A and 33B of the chip carrier 30, on which the measuring chip 10 is mounted, generate a downward magnetic force, and adhere the chip carrier 30 to the top surface 1a. On the other hand, when removing the measuring chip 10, it is possible to make the first magnets 33A and 33B generate an upward magnetic force, and detach it from the top surface 1a easily. As a result, the measuring chip 10 can be installed on and removed from the top surface 1a of the SPR measurement device 1 easily, so that it is possible to exchange measuring chips 10 smoothly.

Furthermore, by inserting the chip carrier 30 into the guide hole 41a of the chip carrier guide 40, it is possible to place the chip carrier 30 at a home position of the SPR measurement device 1. Therefore it is possible to position the measuring chip 10 on the measurement face 4a of the SPR measurement device 1 easily.

Moreover, by moving the chip carrier guide 40 between the first position and the second position selectively, it is possible to change the orientation of the magnetic force generated in the first magnets 33A and 33B of the chip carrier 30. Therefore it is possible to secure and remove the chip carrier 30 to and from the top surface 1a of the SPR measurement device 1 more smoothly.

Furthermore, in the present embodiment, since a repulsive force is used as the magnetic force generated in the first magnets 33A and 33B, it is possible to secure and detach the chip carrier 30 stably.

That is, in contrast to the present embodiment, if the construction is such that an attracting force acts between the first magnets 33A and 33B and the second magnets 42A and 42B, when the first magnets 33A and 33B approach and make contact with the second magnets 42A and 42B, a considerably large force is generated. Therefore it is difficult to separate the two magnets, which makes it difficult to handle. On the other hand, if the two magnets are separated in order to avoid such a situation, the attracting force becomes inadequately small, so a situation can occur in which it is difficult to secure the measuring chip 10. Moreover, if the attracting forces are unbalanced, only one of the pairs of magnets makes contact, so it is difficult to maintain the parallelism of the chip carrier 30 with respect to the top surface 1a of the SPR measurement device 1.

Here, if a repulsive force is used, the two magnets try to separate from each other. Therefore it is easy for the magnetic force to balance, so that it is possible to maintain the parallelism of the chip carrier 30 with respect to the top surface 1a, and the chip carrier 30 can be secured and removed stably.

Even in the case where a repulsive force is used as in the present embodiment, for the repulsive forces generated between the first magnet 33A and the second magnet 42A and the first magnet 33B and the second magnet 42B, it is desirable for the design to consider the magnitude of the magnetic force of the magnets and their locations and the like, in order to achieve a magnetic balance.

Figure 6:
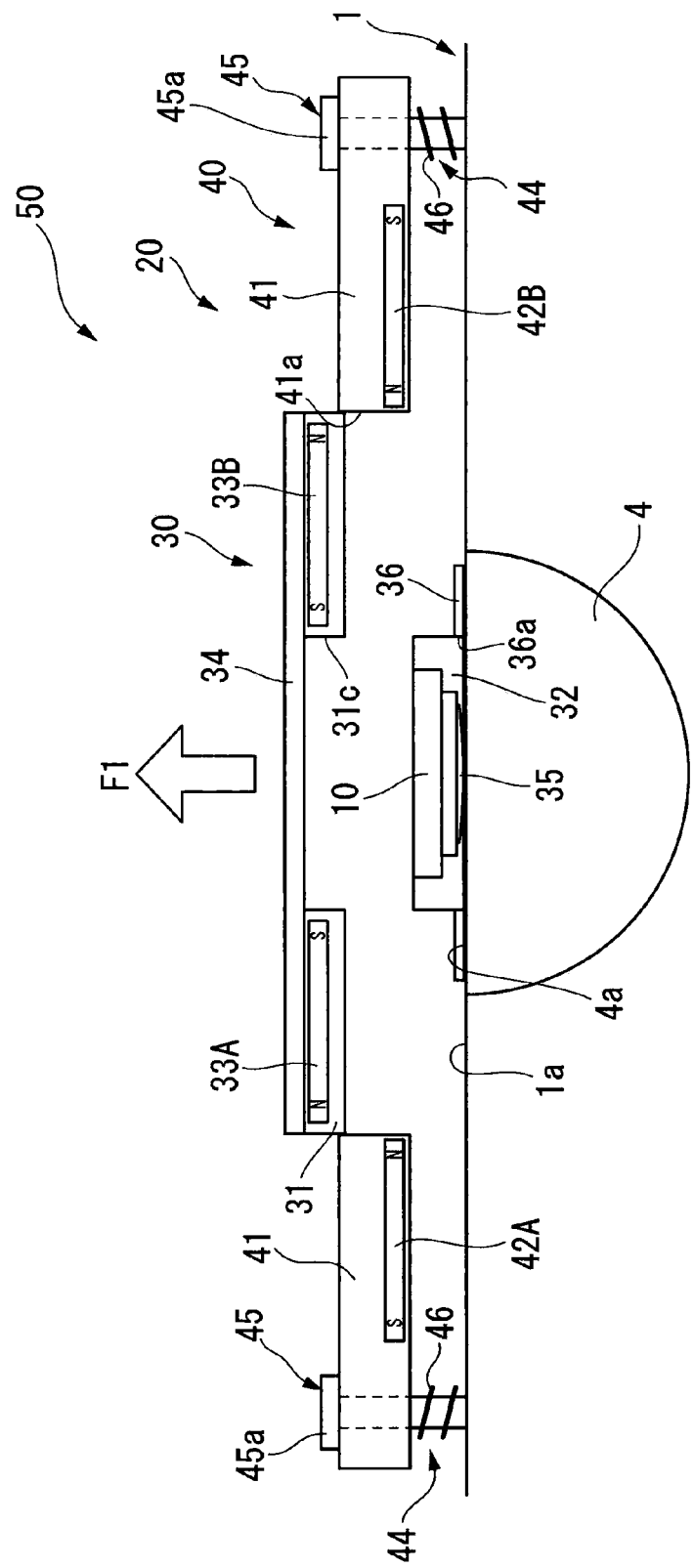
FIG. 6 is a sectional side elevation of an SPR measurement system of a first modified example of the first embodiment.

For a first modified example of the first embodiment as described above, the SPR measurement system 50 may be constructed as shown in FIG. 6 and FIG. 7 for example. In the first modified example, as shown in FIG. 6, a case locating plate 36 is provided on the measurement face 4a of the SPR measurement device 1. A rectangular hole 36a in which the chip case 32 is inserted, is formed approximately in the center of the case locating plate 36.

The chip case 32, in which the measuring chip 10 with the adhered matching film 35 is inserted, is mounted in the rectangular hole 36a. As a result, the measuring chip 10 is mounted at a home position on the measurement face 4a via the matching film 35.

Next, the chip carrier 30 is moved down into the guide hole 41a of the chip carrier guide 40 from above while maintaining the parallelism of the chip carrier 30 and the horizontal face (measurement face 4a) such that the chip carrier 30 is inserted into the guide hole 41a from above the measuring chip 10 and the chip case 32, in a state in which these are not inserted. At this time, the two first magnets 33A and 33B in the chip carrier 30 approach the second magnets 42A and 42B of the guide 40. As a result, an upward force F1 acts on the chip carrier 30 as a whole.

Next, the chip carrier 30 is moved down further against this upward force F1, and as shown in FIG. 7, the chip case 32 mounted on the measurement face 4a is inserted into the through hole 31c of the chip carrier 30. At this time, a downward repulsive force is generated in each of the first magnets 33A and 33B, a downward force F2 acts on the chip carrier 30 as a whole, and the chip carrier 30 is pressed down on the top surface 1a. As a result, the measuring chip 10 is adhered to the measurement face 4a via the matching film 35, and the measuring chip 10 is mounted parallel to the measurement face 4a.

Furthermore, it is possible to remove a measuring chip 10 that is mounted and secured on the top surface 1a of the SPR measurement device 1 from the top face 1a easily by producing an upward force on the chip carrier 30 by moving the chip carrier guide 40 from the first position to the second position as described above.

Next is a description of an SPR measurement system 50 of a second modified example of the first embodiment with reference to FIGS. 8A to 8F. In the second modified example of the first embodiment, elements common with those used in the first embodiment are denoted by the same reference symbols, and their descriptions are omitted.

Figure 8A:
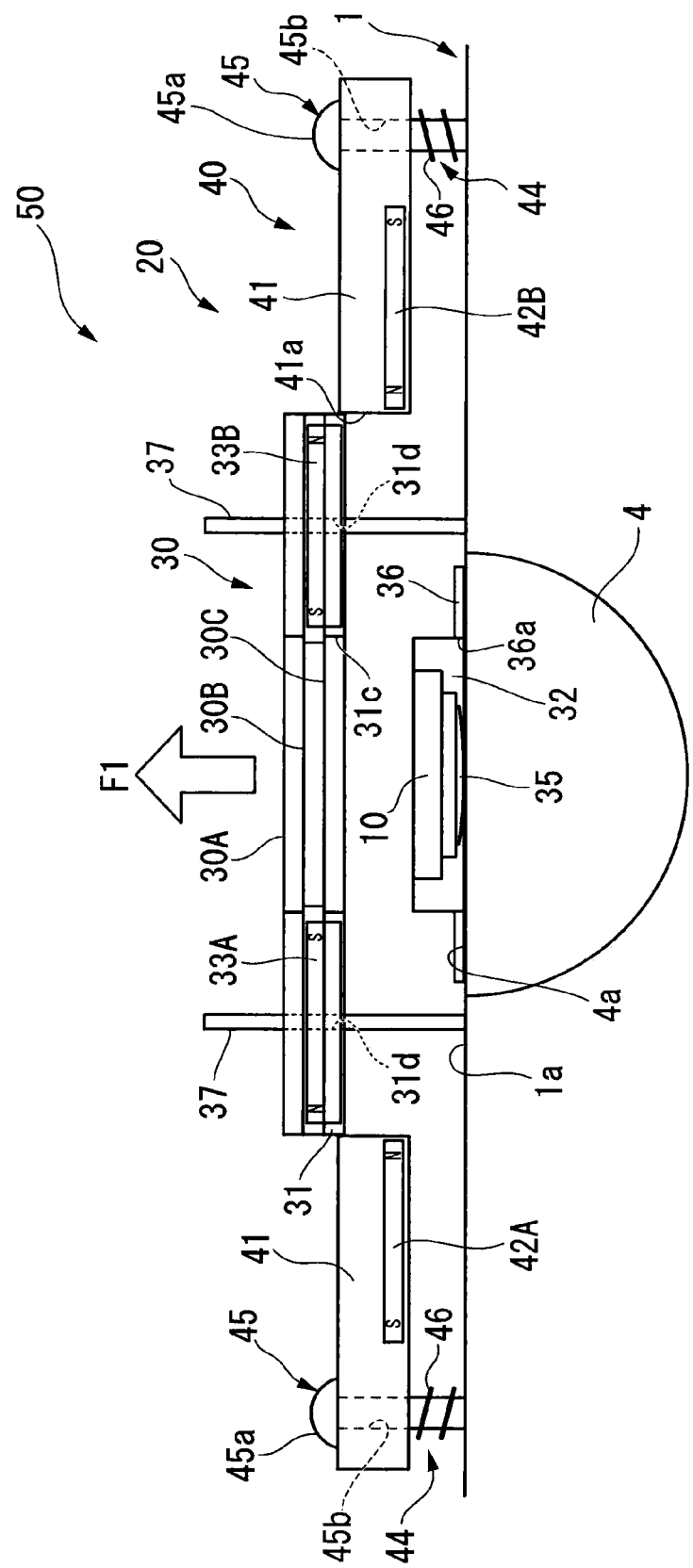
FIG. 8A is a sectional side elevation of an SPR measurement system of a second modified example of the first embodiment.
Figure 8B:
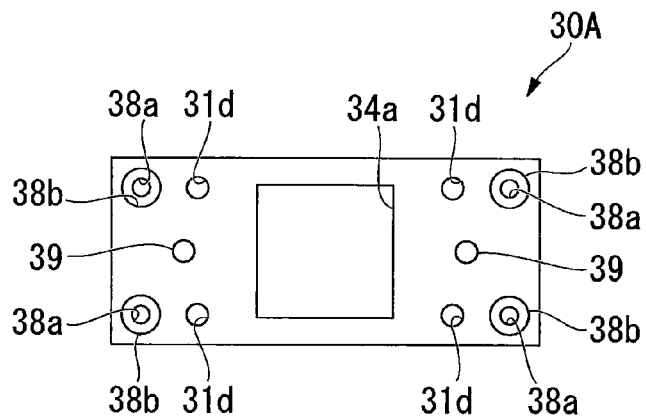
FIG. 8B is a top view of a part of the chip carrier shown in FIG. 8A.
Figure 8C:
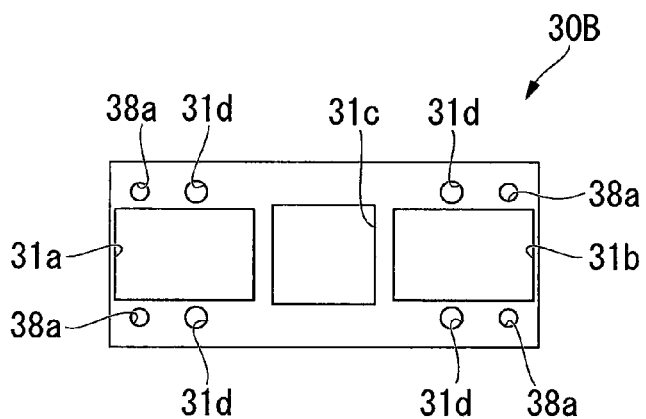
FIG. 8C is top view of a part of the chip carrier shown in FIG. 8A.
Figure 8D:
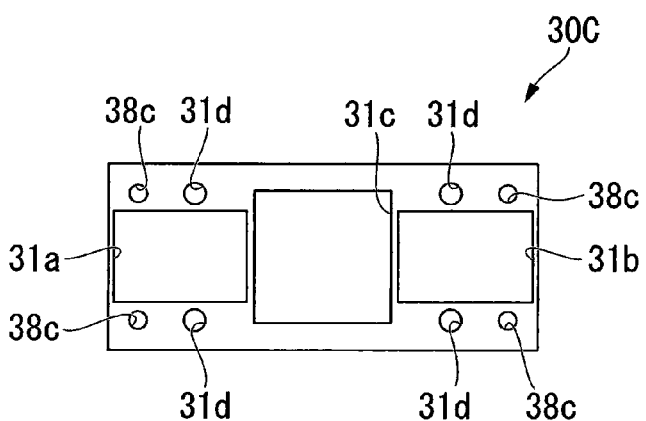
FIG. 8D is a top view of the chip carrier shown in FIG. 8A.
Figure 8E:
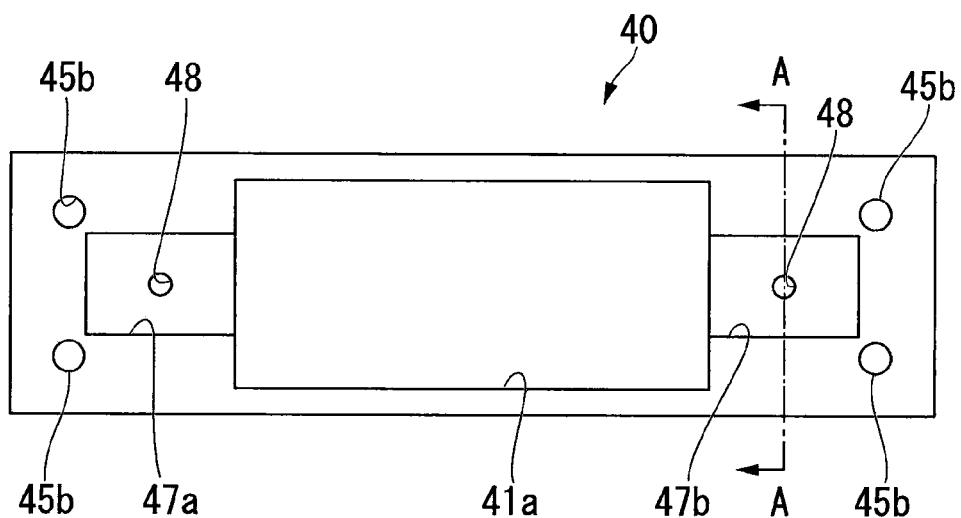
FIG. 8E is a top view of the chip carrier guide shown in FIG. 8A.
Figure 8F:
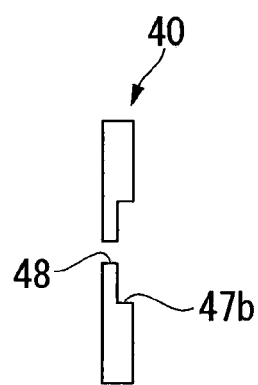
FIG. 8F is a cross-sectional diagram cut along line A-A of FIG. 8E.

FIG. 8A is a sectional side elevation of the second modified example of the first embodiment. FIGS. 8B to 8D are top views of the chip carrier parts 30A to 30C shown in FIG. 8A. FIG. 8E is a top view of the chip carrier guide 40 shown in FIG. 8A. FIG. 8F is a cross-sectional diagram cut along line A-A of FIG. 8E.

The chip carrier 30 of the second modified example of the first embodiment is provided with four guide pillars 37 for guiding the chip carrier 30 as shown in FIG. 8A. The guide pillars 37 are provided in a vertical orientation in areas in the four corners of the chip carrier 30 on the top surface 1a of the SPR measurement device 1. Guide holes 31d are formed in the four corners of the chip carrier 30. The construction is such that by the guide pillars 37 being inserted into the respective guide holes 31d, the chip carrier 30 can move vertically while maintaining itself parallel with the top surface 1a of the SPR measurement device 1.

Next is a detailed description of the chip carrier 30 and the chip carrier guide 40 of the second modified example of the first embodiment, with reference to FIG. 8A to FIG. 8F.

The chip carrier 30 of the second modified example of the first embodiment has chip carrier parts 30A to 30C instead of the housing 31, the chip case 32, and the lid 34 in the first embodiment. The chip carrier 30 is formed by stacking the chip carrier parts 30A to 30C.

Four through holes 38a are provided in the four corners of the chip carrier parts 30A and 30B. Four through holes 38c in which female threads are formed, are provided in the four corners of the chip carrier part 30C. The through holes 38c are provided in areas corresponding to the through holes 38a. Indentations 38b are provided on the top surface side of the through holes 38a in the chip carrier part 30A. The chip carrier parts 30A to 30C are fixed together by screwing screws into the through holes 38a and the through holes 38c such that the screw heads are located in the indentations 38b, and the male threads of the screws and the female threads of the through holes 38c are screwed together.

Furthermore, four guide holes 31d adjacent to the through holes 38a or the through holes 38c are provided in the chip carrier parts 30A to 30C. Guide pillars 37 are inserted into the guide holes 31d.

Through holes 39 are provided in the chip carrier part 30A at locations above the cavities 31a and 31b in the state in which the chip carrier parts 30A to 30C are fixed together. Female threads are formed in the through holes 39. Through holes are provided at locations in the first magnets 33A and 33B that correspond to the through holes 39 in the state in which they are inserted in the cavities 31a and 31b. The first magnets 33A and 33B are secured in the chip carrier 30 by inserting screws into the through holes 39 of the chip carrier part 30A and the through holes of the first magnets 33A and 33B such that the male threads of the screws and the female threads of the through holes 39 are screwed together.

Four through holes 45b are provided in the four corners of the chip carrier guide 40. Bolts 45 are inserted into the through holes 45b. Cavities 47a and 47b, which are approximately rectangular in plan view, are provided at the two sides in the longitudinal direction of the guide hole 41a of the chip carrier guide 40. Through holes 48 in which female threads are formed are provided in the centers of the cavities 47a and 47b. Through holes are provided at locations in the second magnets 42A and 42B that correspond to the through holes 48 in the state in which they are inserted into the cavities 47a and 47b. The second magnets 42A and 42B are secured in the chip carrier guide 40 by screwing screws into the through holes 48 of the chip carrier guide 40 and the through holes of the second magnets 42A and 42B such that the male threads of the screws and the female threads of the through holes 48 are screwed together.

In the second modified example of the first embodiment, by providing the guide pillars 37 and guide holes 31d in this manner, it is possible to move the chip carrier 30 easily. Furthermore, when the chip carrier guide 40 is moved from the first position to the second position such that the chip carrier 30 is removed from the top surface 1a, an upward force is generated in the chip carrier 30, and as shown in FIG. 8A, the chip carrier 30 can be floated above the guide hole 41a stably. As a result, the chip carrier 30 does not jump off the SPR measurement device 1 unexpectedly, and furthermore it is possible to reliably prevent the specimen in the measuring chip 10 from splashing contamination on the surroundings.

Figure 9:
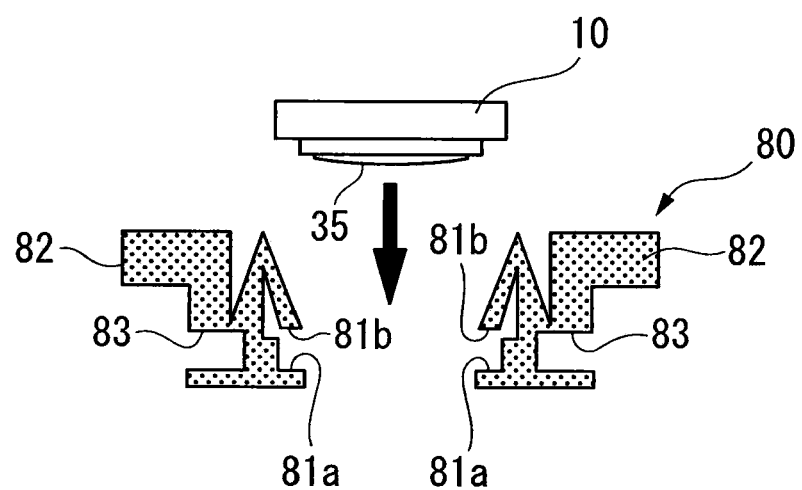
FIG. 9 is a sectional side elevation of a chip case in a second embodiment.
Figure 10A:
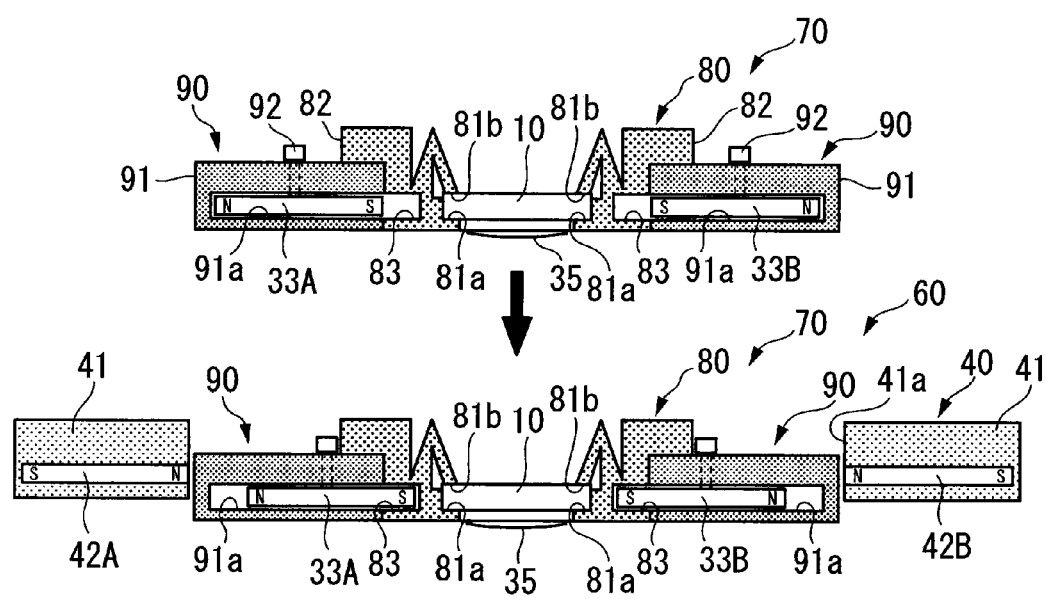
FIG. 10A is a sectional side elevation of a measuring chip installation/removal device of the second embodiment.
Figure 10B:
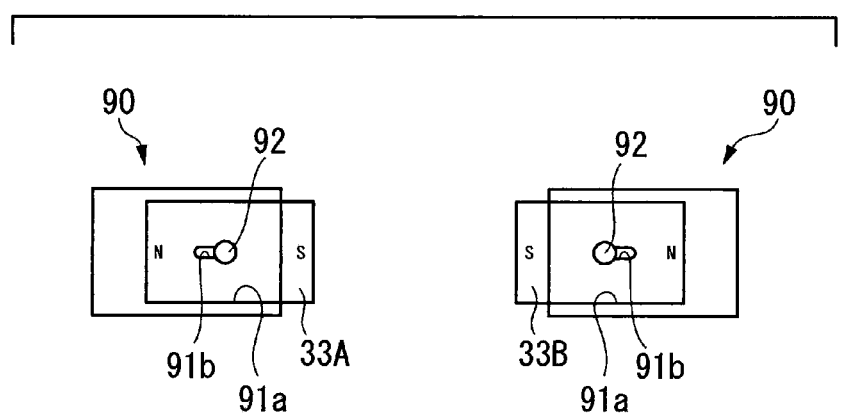
FIG. 10B is a plan view of a pair of magnet cases in the second embodiment.

Next is a detailed description of a second embodiment of the present invention with reference to FIG. 9, FIG. 10A, and FIG. 10B. In FIG. 9, FIG. 10A, and FIG. 10B, the constructions other than the chip carrier 70 are the same as in the first embodiment.

The chip case 80 as shown in FIG. 9, is square and tubular, and is open in the vertical direction. A chip mounting section 81a is formed in the bottom opening of the chip case 80, and is projected inwards in the radial direction. The measuring chip 10 is mounted in the chip mounting section 81a such that its bottom face is flush with the bottom face of the chip case 80, and it is exposed on the bottom face of the chip case 80. The top surface of the measuring chip 10 mounted in the chip mounting section 81a is supported by a chip holding section 81b.

Flange sections 82 are formed around the top edge of the chip case 80, and are projected in the left and right directions as in FIG. 9. Concave grooves 83 are formed below the flange sections 82, and are indented inwards in the radial direction from the side face of the chip case 80.

As shown in FIG. 10A, a pair of magnet cases 90 is arranged on the left and right sides of the chip case 80. The first magnets 33A and 33B are inserted into the pair of magnet cases 90 such that they can slide and project towards the side faces of the chip case 80.

To be specific, the magnet cases 90 include magnet pockets 91a, which are cuboid and open towards the sides of the magnet case bodies 91. The magnet cases 90 are assembled with the first magnets 33A and 33B being inserted into the magnet pockets 91a from their north pole sides. In the magnet cases 90, slits 91b (refer to FIG. 10B) are formed, which pass through the top surfaces of the magnet cases 90 and the magnet pockets 91a in the vertical direction, and extend in the sliding directions of the first magnets 33A and 33B. Levers 92, which are connected to the first magnets 33A and 33B such that they pass through the slits 91b, protrude upwards from the magnet cases 90. The first magnets 33A and 33B can be slid in the horizontal direction by moving the levers 92 manually within the range in which the slits 91b are formed.

Using the following procedure, the chip case 80 and the magnet cases 90 can be fixed together, and the measuring chip 10 can be introduced to the top surface 1a of the SPR measurement device 1.

Firstly, a matching film 35 is adhered on the bottom of the measuring chip 10. Afterwards, the measuring chip 10 is secured in the chip case 80.

Next, as shown in FIG. 10A, the magnet cases 90 are arranged on the left and right sides of the chip case 80 such that the openings of the magnet pockets 91a face towards the chip case 80. At this time, the magnet pockets 91a and the concave grooves 83 of the chip case 80 are in a continuous state. Furthermore, the pair of flange sections 82 of the chip case 80 are mounted on the magnet cases 90.

In the state in which the chip case 80 and the magnet cases 90 are so arranged, the plan view shape of the two combined together (that is, the plan view shape of the chip carrier 70) is approximately the same as the plan view shape of the guide hole 41a of the chip carrier guide 40.

The chip case 80 and the magnet cases 90 are introduced into the guide hole 41a of the chip carrier guide 40 while maintaining the arrangement of the chip case 80 and the magnet cases 90. At this time, the two first magnets 33A and 33B in the magnet cases 90 approach the second magnets 42A and 42B of the chip carrier guide 40. As a result, forces are generated in the first magnets 33A and 33B that separate them from the second magnets 42A and 42B due to the interaction of the north poles of the first magnets 33A and 33B and the north poles of the second magnets 42A and 42B. Due to this, the first magnets 33A and 33B in the magnet cases 90 slide towards the sides of the chip case 80 (refer to FIG. 10A and FIG. 10B), and are inserted into the concave grooves 83 of the chip case 80. As a result, the chip case 80 and the magnet cases 90 are secured and fixed together.

In this manner, the chip case 80 and the magnet cases 90 are secured, and in the case where the assembled chip case 80 is mounted on the top surface 1a of the SPR measurement device 1, it is pressed down on the top surface 1a by a downward repulsive force generated in the first magnets 33A and 33B.

A method is described in which the chip carrier 70 is removed from the top surface 1a in such a state. During removal, an upward repulsive force is generated in the first magnets 33A and 33B by moving the chip carrier guide 40 from the first position to the second position. As a result, it is possible to detach the chip carrier 70 from the top surface 1a easily. On the other hand, when the chip carrier 70 is removed from the top surface 1a of the SPR measurement device 1, and separated from the chip carrier guide 40 in this manner, repulsive forces are no longer generated in the first magnets 33A and 33B. Therefore, by moving the levers of each of the magnet cases 90 manually, and extracting the first magnets 33A and 33B from the concave grooves 83 of the chip case 80, it is possible to separate the chip case 80 and the magnet cases 90.

In this manner, in a measuring chip installation/removal device 60 of the second embodiment, the chip case 80 and the magnet cases 90 are fixed together by the first magnets 33A and 33B being inserted into the concave grooves 83 respectively, only when the chip carrier 70 including the chip case 80 and the magnet cases 90 is mounted on the top surface of the SPR measurement device (omitted in FIG. 10A).

Accordingly, when measurement is not being performed, the chip carrier 70 can be separated into the chip case 80 and the magnet cases 90. Therefore it is possible to improve the handling of the chip carrier 70. On the other hand, when measurement is being performed, it is possible to position and lock the measuring chip 10 and the SPR measurement device 1 easily.

As above, the measuring chip installation/removal device, the SPR measurement system, and the measuring chip installation/removal method according to the embodiments of the present invention are described in detail with reference to the drawings. However, specific constructions are not limited to the embodiments, and any design change that does not depart from the gist of the present invention is included.

That is, the technical essence of the present invention is the securing and removing of the measuring chip 10 to and from the top surface 1a of the SPR measurement device 1 employing the support of magnetic force, and any embodiment is included provided it has these characteristics.

For example, in the present embodiment, a case is described in which a pair of first magnets 33A and 33B and a pair of second magnets 42A and 42B are provided. However, this is not a limitation, and the number of sets is arbitrary. In any case, it is desirable to choose and locate the magnets such that the repulsive force generated in each magnet is balanced.

Moreover, the shapes of the first magnets 33A and 33B and the second magnets 42A and 42B are not limited to the shapes shown in the embodiments. For example, ring shaped magnets in two concentric circles may be used. In this case, for the ring shaped magnets, magnets are used whose opposing magnetic poles are on their outside diameter sides and their inside diameter sides, and one ring shaped magnet is located such that it passes through the inside diameter side of the other magnet with their axes coincident. The measuring chip 10 is secured and removed by the magnetic force generated in the two magnets.

Furthermore, the construction is not only one that uses repulsive forces generated between the first magnets 33A and 33B and the second magnets 42A and 42B, but may also be such that the measuring chip 10 is secured and removed using attracting forces.

Moreover, in the first and second embodiments, examples are described in which repulsive forces between the north poles of the first magnets 33A and 33B and the second magnets 42A and 42B are used. However, it may also be that the measuring chip 10 is secured and removed by repulsive forces between south poles by reversing the orientations of the pairs of magnets.

The first magnets 33A and 33B, and the second magnets 42A and 42B, are not limited to permanent magnets, and may be electromagnets.

INDUSTRIAL APPLICABILITY

The present invention can be used for a measuring chip installation/removal device, an SPR measurement device on which it is mounted, and a measuring chip installation/removal method in which the measuring chip installation/removal device is used. According to the measuring chip installation/removal device, the SPR measurement device, and the measuring chip installation/removal method, by making the chip carrier on which the measuring chip is mounted, generate magnetic force in an appropriate direction, it is possible to install and remove a measuring chip to and from the top surface of the SPR measurement device easily and it is possible to exchange measuring chips easily.

REFERENCE SYMBOLS

1 SPR measurement device
2 Light source
3 Incident side lens
4 Prism
4a Measurement face
5 Light detecting section
10 Measuring chip
11 Metal thin film
20 Measuring chip installation/removal device
30 Chip carrier
30A to 30C Chip carrier parts
33A First magnet
33B First magnet
35 Matching film
36 Case locating plate
37 Guide pillar
40 Chip carrier guide
41a Guide hole
42A Second magnet
42B Second magnet
44 Movable mechanism
46 Coil spring (energizing member)
50 SPR measurement system
60 Measuring chip installation/removal device
70 Chip carrier
80 Chip case
83 Concave groove
90 Magnet case

The invention claimed is:

1. A measuring chip installation/removal device that secures and removes a measuring chip to and from the top surface of an SPR measurement device that measures a specimen in the measuring chip by surface plasmon resonance, the measuring chip installation/removal device comprising:
   a chip carrier on which the measuring chip is mounted;
   a chip carrier guide that guides the chip carrier on the top surface; and
   a first magnet provided in the chip carrier, and a second magnet provided in the chip carrier guide,
   orientation of a force created by the magnet's magnetic fields received by the first magnet from the second magnet being reversed by displacing the chip carrier guide from a first position at which the chip carrier guide is separated upwards from the top surface to a second position that is adjacent the top surface, so that the chip carrier is removed from the top surface.

2. The measuring chip installation/removal device according to claim 1,
   wherein the chip carrier guide has a plate shape extending along the top surface, and has a guide hole which passes through the chip carrier guide in a thickness direction thereof, and in which the chip carrier is inserted.

3. The measuring chip installation/removal device according to claim 1, wherein the magnetic field create a repulsive force generated between the first magnet and the second magnet.

4. The measuring chip installation/removal device according to claim 3,
   wherein there is provided an energizing member that urges the chip carrier guide toward the first position from the second position,
   the second magnet of the chip carrier guide in the first position is located above the first magnet of the chip carrier mounted on the top surface, and
   the second magnet of the chip carrier guide in the second position is located below the first magnet of the chip carrier mounted on the top surface.

5. The measuring chip installation/removal device according to claim 4,
   wherein the chip carrier includes a chip case in which the measuring chip is secured, and a magnet case that is located at a side of the chip case, and that retains the first magnet such that it slide and project in a horizontal direction, and
   when the repulsive force is generated in the first magnet, the first magnet slides so as to enter a concave groove provided in a side face of the chip case.

* * * * *

UNITED STATES PATENT AND TRADEMARK OFFICE
CERTIFICATE OF CORRECTION

| | |
|---|---|
| PATENT NO. | : 8,531,658 B2 |
| APPLICATION NO. | : 13/125279 |
| DATED | : September 10, 2013 |
| INVENTOR(S) | : Tsutomu Horiuchi et al. |

It is certified that error appears in the above-identified patent and that said Letters Patent is hereby corrected as shown below:

On the Title Page

In item (87), the PCT Pub. Date should indicated -- May 6, 2010 --.

Signed and Sealed this
Fourteenth Day of January, 2014

Michelle K. Lee
*Deputy Director of the United States Patent and Trademark Office*